United States Patent [19]
Bartscher et al.

[11] 4,192,836
[45] Mar. 11, 1980

[54] RESPIRATORY GAS HUMIDIFIER

[75] Inventors: Wolfgang Bartscher, Langen; Jürgen Sachtler; Roland Schultner, both of Lübeck, all of Fed. Rep. of Germany

[73] Assignee: Drägerwerk Aktiengesellschaft, Fed. Rep. of Germany

[21] Appl. No.: 951,037

[22] Filed: Oct. 13, 1978

[30] Foreign Application Priority Data

Oct. 22, 1977 [DE] Fed. Rep. of Germany ....... 2747488

[51] Int. Cl.$^2$ ................. B01F 3/04; A61M 15/00
[52] U.S. Cl. ................. 261/142; 128/200.11; 261/64 D; 261/120; 261/DIG. 65
[58] Field of Search ............... 128/185,186,192–194; 261/64 D, 120, 121 R, 123, 142, 129, DIG. 65; 291/271–276

[56] References Cited

U.S. PATENT DOCUMENTS

| 162,543 | 4/1875 | Foster | 261/120 |
|---|---|---|---|
| 1,411,950 | 4/1922 | Wyatt | 261/120 |
| 1,533,719 | 4/1925 | Woolf | 261/120 X |
| 2,709,577 | 5/1955 | Pohndorf et al. | 128/185 X |
| 2,862,354 | 12/1958 | Barnhart | 261/120 X |
| 3,045,990 | 7/1962 | Keenan, Jr. | 261/120 |
| 3,573,203 | 3/1971 | Kaelin | 261/120 X |
| 3,724,454 | 4/1973 | Brown | 261/DIG. 65 |
| 3,982,095 | 9/1976 | Robinson | 261/DIG. 65 |
| 3,990,441 | 11/1976 | Hoyt et al. | 261/DIG. 65 |

FOREIGN PATENT DOCUMENTS

| 2512607 | 10/1975 | Fed. Rep. of Germany | 128/186 |
|---|---|---|---|
| 2512732 | 10/1975 | Fed. Rep. of Germany | 128/186 |

*Primary Examiner*—Richard L. Chiesa
*Attorney, Agent, or Firm*—McGlew and Tuttle

[57] ABSTRACT

A respiratory gas humidifier comprises a closed water reservoir having a water level therein which is maintained so that it does not vary beyond a great change in the height level. A guide nipple is mounted on the bottom of the reservoir and extends upwardly in the water and an inlet conduit extends into the top of the reservoir and overlies the guide nipple, but is spaced therefrom. A float is provided with a sleeve or hub portion which is guided on the guide nipple and the inlet conduit and includes a float portion which maintains the lower end of the hub portion below the level of the water in the reservoir. Respiratory gases are guided through the inlet conduit and to a space between the hub portion of the float and the guide nipple so that it always exits into the water at the same level and bubbles upwardly through the water and out through an outlet for use by a patient. In accordance with the method of the invention, respiratory gases are directed into a liquid reservoir containing water which is heated to a controlled temperature and it is permitted to bubble upwardly through the liquid at substantially the same height of upward bubbling travel and, wherein the height is controlled by a float so that the gas is always delivered at the same level below the surface of the water for upward bubbling therethrough.

7 Claims, 2 Drawing Figures

RESPIRATORY GAS HUMIDIFIER

FIELD AND BACKGROUND OF THE INVENTION

This invention relates to respiratory devices in general and, in particular, to a new and useful device and process for humidifying and warming respiratory gas.

DESCRIPTION OF THE PRIOR ART

During the treatment of patients with respirators, the necessary moist and warm atmosphere must be maintained in the respiratory tracts. This should be possible independently of the quantities of respiratory gas and of pressure changes occurring during the treatment.

The known processes for humidifying and warming the treatment air in respirators differ with the type of humidification. One type has vaporizers in which water evaporates directly by heating to the boiling point and the steam is then mixed with the treatment air. The method of the respirator type consists in passing the treatment gases through the water to cause them to bubble through. During the bubbling, the gas bubbles take up the necessary moisture and the device is referred to as a "bubbler."

The humidifier operating on the vaporization principle requires a complicated temperature control for heating the water and also a gas mixing device which must mix satisfactorily at greatly variable quantities of respiratory gas.

The "bubblers" are simpler in design. This is particularly true in respect to the heating of the treatment gas. A problem is the difficulty of maintaining the constant bubbling height necessary for uniform humidification.

In a known process for humidification and heating, the respiratory gas is injected into the water from the outside through notches between the side wall and the bottom of the water receiver and is then shunted to the patient above the water surface in a humidified state. The quantity of water consumed from the receiver is continuously added from the reservoir. The temperature is regulated as a function of the exit temperature of the humidified respiratory gas. The water supply is replenished from a water storage tank. To this end, the tank has a neck section protruding into the water supply. Additional water flows in whenever the water level in the reservoir clears the neck section. The constant bubbling height necessary for a uniform humidification of respiratory gas quantities, which may vary, cannot be achieved with this process. The continuous influx of water from the reservoir presupposes a constant pressure head in the reservoir. However, the head fluctuates due to the alternating rise and fall of the water level in accordance with the frequency of respiration, as a result of the varying pressure heads. The pressure is in equilibrium with the water column and with the air space in the water storage tank. Upon changes of the treatment pressure to lower values, or upon disconnection, a corresponding quantity of water drains from the storage tank to pressure equalization and completely alters conditions in the water receiver, as described in German Patent DT-OS No. 2,512,607.

Another known humidification device for respiratory gases includes a water tank having a diffuser adjacent the bottom thereof which is connected with the respiratory gas inlet. As a result of sufficiently small orifices in the diffusor plate, a respiratory gas pocket forms in the diffusor arrangement. A ball-type check valve under a respiratory gas inlet nipple prevents the water from rising into the nipple. After bubbling through the water, the respiratory gas is discharged through an outlet arrangement. The outlet arrangement has a separator protruding into the water in which the impurities, such as, contaminating components, are separated out of the return flow condensate. The water level in the tank and, hence, the bubbling height is monitored by a photoelectric sensor arrangement. Heating of the water is effected by a heating system located at the bottom and outside of the water tank. With this device, which is made complicated by the photoelectric sensor arrangement, it is also not possible to maintain the bubbling height continuously at the same level. The sensor only functions to signal when the water level falls below a given value. After the water tank has been filled up, the greater bubbling height must be overcome, which then diminishes again to a minimum height, varying continually. See German Patent DT-OS No. 25 12 732.

SUMMARY OF THE INVENTION

In accordance with the present invention, for all treatment conditions, a respiratory gas having a defined moisture and desired temperature is supplied to a patient, using an apparatus which is easy to clean and to disinfect.

With the use of a float in a liquid reservoir, the same bubbling height, i.e., the path through the water, which for all treatment conditions is a precondition for equal humidification, is ensured. With the invention, the humidifying of the respiratory gas is independent of any volume variations in the respiratory gas caused by the small differences in pressure. An apparatus for such humidifying requires only a few simple components which can be reliably controlled. The water replenishment can be solved without problem by means of known valve systems.

The humidification device, consisting in an advantageous manner of few components, fulfills every safety demand in operation. The components are easy to manufacture, e.g., by plastic injection molding. The device can be taken apart for cleaning and disinfection without difficulty and without special knowledge and can be reassembled just as easily later on. The invariability of the bubbling cross-sections along with the constant bubbling height ensure an always uniform humidification of the respiratory gas passed therethrough. The device includes a float ring, which is divided into chambers so as to permit variation of the design of the apparatus and also the construction of portable units. Warming is effected in a known manner by control of the water temperature. Operating safely and accurately, the same heating system, by additional warming of the humidified respiratory gas, fulfills the obvious requirement of preventing contamination of the apparatus and of the water by back-flowing condensate.

Accordingly, an object of the invention is to provide a respiratory gas humidifier which includes a reservoir containing a water which is heated to a control temperature and includes conduit means extending downwardly into the water which includes a lower portion having an exit defined below the water surface by a sleeve portion of a float which floats on the water to maintain the sleeve exit at the same level therebelow so that the water may bubble upwardly through the water at a uniform height of bubble travel before it is delivered outwardly from the reservoir to the patient.

Another object of the invention is to provide a method of treating respiratory gases which comprises directing the gases into a reservoir containing water heated to a predetermined temperature below the level of the water and including controlling the depth at which the gases are delivered below the level of the water by a float which rides on the water.

A further object of the invention is to provide a respiratory gas humidifier which is simple in design, rugged in construction and economical to manufacture.

The various features of novelty which characterize the invention are pointed out with particularity in the claims annexed to and forming a part of this disclosure.

For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
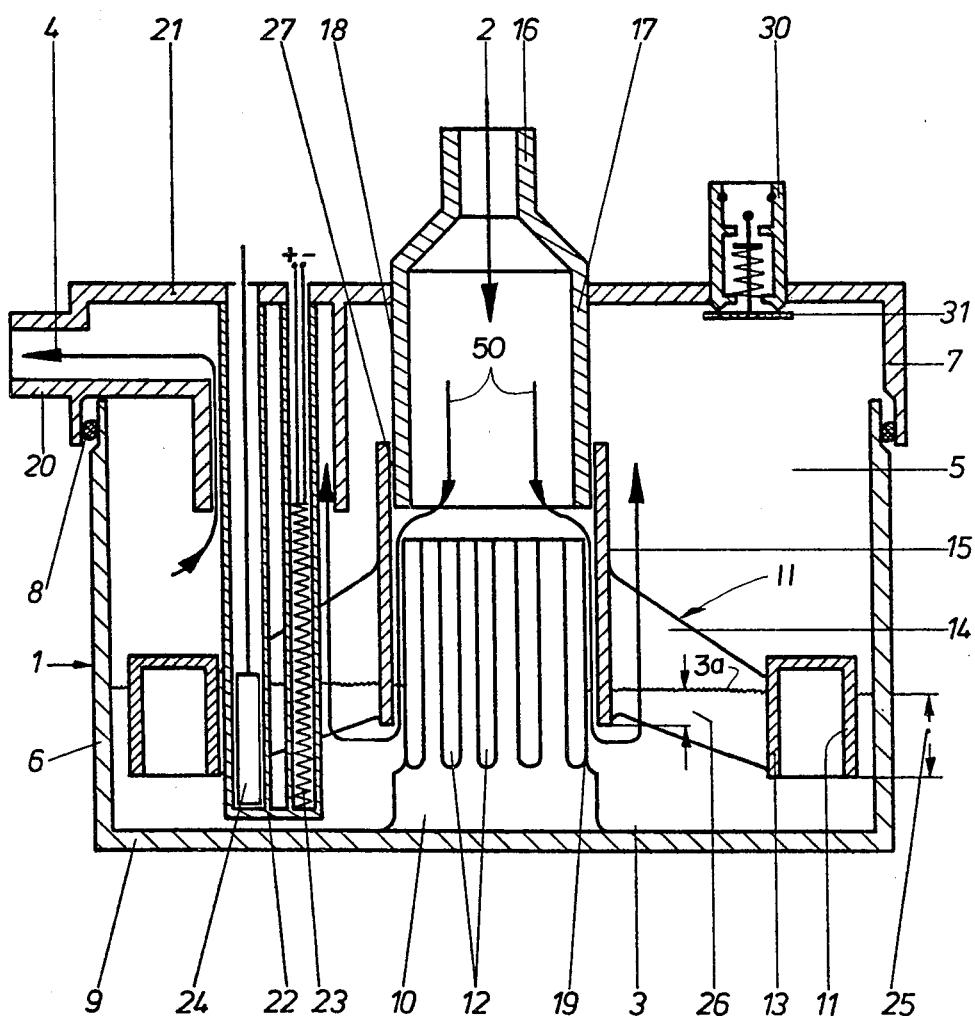
FIG. 1 is a transverse sectional view of a respiratory gas humidifier constructed in accordance with the invention.
Figure 2:
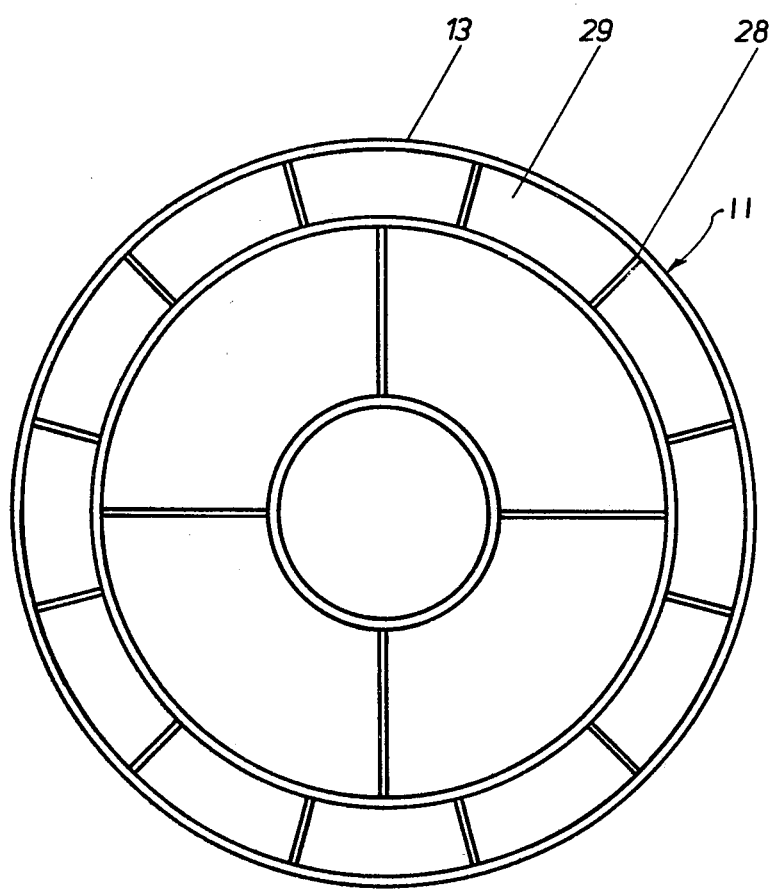
FIG. 2 is a bottom plan view of the floatable gas passage used in the reservoir shown in FIG. 1.

Referring to the drawings in particular, the invention embodied therein, comprises, a reservoir, generally designated 1, having a water 3 therein which is maintained at a level 3a which does not vary to any great amounts and which, for example, may be obtained by manual replenishment or by an automatic means for insuring at least that it does not fall below a predetermined level.

The temperature of the water is maintained so that the water is in a heated state and this heating is carried out by heating means contained in a tubular mount 22 and which includes a temperature sensor 24 connected to an electrical resistance heater 23 so as to maintain heating thereof whenever the water temperature falls below a predetermined amount.

In accordance with the invention, respiratory gases are delivered through a conduit 16 in the direction of the arrow indicated at 2 and they are delivered by conduit means, including a tubular portion 17 and a hub or sleeve portion 15 of a float, generally designated 11, in cooperation with a guide nipple 10 which is mounted on a bottom 9 of the reservoir so that the lower end of a sleeve portion 15 of the float is maintained at the same level below the surface 3a during the operation of the device. With such an arrangement, the respiratory gases move as indicated by arrows 50 downwardly between the nipple 10 and the sleeve 15, such as through elongated indentations or slots 12 and exit around the bottom of sleeve 15 so that they are permitted to flow upwardly through the liquid level at the same bubbling height 26 regardless of the level 3a of the water.

The respiratory gas to be humidified and heated is introduced into the humidifier 1 in direction 2 through an inlet tube 16 and is bubblingly passed through heated water 3, leaving it through an outlet 20 in direction 4. The respirator includes a tank 5 of a transparent material, such as plastic, having a bottom part 6 and a cover 7. Cover 7, which is easy to remove, is sealed relative to the bottom part 6 by a seal 8. A guide nipple 10 is centered on the inside on a bottom wall 9 of the bottom guide sleeve or part 6, and a float 11 having a hub portion 15 is movably guided on the nipple for upward and downward movement. The outer surface of the guide nipple 10 is provided with fine slots 12. Float 11 has a float ring portion 13 opening downwardly toward the bottom and forming in annular cavity. The float ring portion 13 is connected through radial bridge pieces 14 with the guide sleeve 15 which, in turn, is movable on the guide nipple 10. The cavity of the float ring 13 is subdivided by cross-pieces 28 into individual chambers 29. The escape of the carrying gas when the humidifier is in an inclined position is thereby prevented.

The cover 7 is axially traversed by the respiratory gas inlet tube 16. The tube 16 widens in the interior of the tank to a guide pipe portion 17 having an outside diameter 18 which is the same as the outside diameter 19 of the guide nipple 10. Sleeve 15 is guided not only on the guide nipple 10 but also on the guide pipe portion 17. Externally, the cover 7 is traversed by the respiratory gas outlet 20. On the roof 21 of cover 7, there is a tubular mount 22 extending inwardly from the roof 21 to near the bottom 9 of bottom part 6. A heating system 23, such as an electric resistance heater, and a temperature sensor 24, are arranged in the mount 22.

Float 11 floats on the surface of the water 3 at equal depth of immersion 25, independently of the height of the water level. A bubbling height 26 of always constant length results from the depth of immersion of the guide sleeve 15 movably guided on the guide nipple 10.

As the respiratory gas passes from the inlet nipple 16, its steam is divided by the fine slots 12 into gas bubbles, which then absorb moisture from the water by their large surface. The respiratory gas is forced through the slots 12. The guide sleeve 15 engages over the guide pipe 17 and prevents a disturbing flow of gas between the guide pipe 17 and the sleeve 15. A moisture seal in any gap 27 between guide pipe 17 and sleeve 15 is obtained by a film of water which is created by the bubbling effect of the gases moving through the heated water.

The temperature of the water is controlled by the temperature sensor 24 which is connected to actuate the heater 23. The mount 22, which upon heating of the water by the heating system 23 immediately heats up somewhat more intensely, warms the outflowing respiratory gas additionally. The breathing hose to the patient which is connected to outlet 20 is thereby kept free of condensate. The feed of water into tank 5 occurs through the nipple 30, the spring-loaded valve 31 being in an opened position. Other solutions, e.g., by automatic valve operation by float 11 and then inflow of the permanently available water, are obvious technical solutions.

The simple design of the few components of the humidifier permits the cleaning and disinfection of the device without any problems.

While a specific embodiment of the invention has been shown and described in detail to illustrate the application of the principles of the invention, it will be understood that the invention may be embodied otherwise without departing from such principles.

What is claimed is:

1. A respiratory gas humidifier, comprising, a closed water reservoir having a water level therein, a predetermined level which may vary during operation, means for heating the water to a predetermined temperature, an outlet for the respiratory air extending out of the reservoir above the level of the liquid and inlet conduit means extending into the reservoir and including a float floating on the water having a sleeve portion defining a conduit within the sleeve portion for the flow of the respiratory air which is maintained by the float at a constant depth below the level of the liquid and opens into the liquid at the depth below the liquid level, whereby, the respiratory air which is delivered through said inlet conduit means exits into the water for upward bubbling therethrough at a constant bubbling height through the water, said float including an annular float portion surrounding said sleeve, said inlet conduit means including a tubular conduit portion extending downwardly into the reservoir from the top thereof, said sleeve being guided on said downwardly extending portion in substantially sealing engagement therewith.

2. A respiratory gas humidifier, comprising, a closed water reservoir having a water level therein, a predetermined level which may vary during operation, means for heating the water to a predetermined temperature, an outlet for the respiratory air extending out of the reservoir above the level of the liquid and inlet conduit means extending into the reservoir and including a float floating on the water having a sleeve portion defining a conduit within the sleeve portion for the flow of the respiratory air which is maintained by the float at a constant depth below the level of the liquid and opens into the liquid at the depth below the liquid level, whereby, the respiratory air which is delivered through said inlet conduit means exits into the water for upward bubbling therethrough at a constant bubbling height through the water, a guide nipple on the bottom of said reservoir, said sleeve portion of said inlet conduit means being guided on said guide nipple, said guide nipple and said sleeve portion being constructed to define a space therebetween into the water and around the lower end of the sleve portion.

3. A respiratory gas humidifier, comprising, a closed water reservoir having a water level therein which varies in height above the bottom of said reservoir, a guide nipple mounted on the bottom of said reservoir and extending upwardly in the water, means for heating the water to maintain it at a predetermined temperature, an outlet out of said reservoir located above said water level therein, an inlet conduit extending into the top of said reservoir and terminating above said guide nipple, a float having a hub portion engaged around and guided for upward and downward movement on said guide nipple and said nlet conduit and being substantially sealed with said inlet conduit and defining a respiratory gas flow passage between said nipple and said hub portion, said float having a float portion floating on the water and supporting said hub portion so that it extends a substantially constant distance below the surface of the water, the respiratory gas being directed from said inlet conduit between said guide nipple and said hub portion and into the water at a constant level below the surface thereof to bubble upwardly through the water and exit through said outlet.

4. A respiratory gas humidifier, as claimed in claim 3, wherein said float portion comprises a float ring disposed around said hub portion and connected to said hub portion, said float ring being opened downwardly into the water.

5. A respiratory gas humidifier, as claimed in claim 4, wherein said float ring includes a cavity therein and cross-piece means subdividing said cavity into individual chambers.

6. A respiratory gas humidifier, as claimed in claim 4, wherein said reservoir includes a bottom portion and a cover adapted to sealingly engage with said bottom portion, a mount mounted on said cover carrying said means for heating the water therein comprising a tubular member extending downwardly from said cover into said reservoir to below the level of the liquid therein, said heating means also including an electric heater and temperature sensing means connected to said heater for actuating said heater to heat the water when it falls below a predetermined temperature.

7. A respiratory gas humidifier, as claimed in claim 3, wherein said reservoir is made of transparent material.

* * * * *